United States Patent
Mugasimangalam

(10) Patent No.: US 6,544,741 B1
(45) Date of Patent: Apr. 8, 2003

(54) SEQUENCE SPECIFIC AND SEQUENCE NON-SPECIFIC METHODS AND MATERIALS FOR CDNA NORMALIZATION AND SUBTRACTION

(75) Inventor: Raja C. Mugasimangalam, Bangalore (IN)

(73) Assignee: Quark Biotech, Inc., Cleveland, OH (US)

( * ) Notice: Subject to any disclaimer, the term of this patent is extended or adjusted under 35 U.S.C. 154(b) by 0 days.

(21) Appl. No.: 09/614,614

(22) Filed: Jul. 12, 2000

(51) Int. Cl.[7] .............................. C12Q 1/68; C12P 19/34
(52) U.S. Cl. ...................... 435/6; 435/91.1; 435/91.2; 435/91.21; 435/91.41; 435/91.5; 435/91.51
(58) Field of Search .................. 435/6, 91.2, 91.21, 435/91.5, 91.51, 91.1, 91.41

(56) References Cited

U.S. PATENT DOCUMENTS 6,265,165 B1 * 7/2001 Xu et al. ...................... 435/6

OTHER PUBLICATIONS

Soares et al. (1994) Proc. Natl. Acad. Sci. USA 91: 9228–32.

Normalizing cDNA libraries using the Eppendorf Thermomixer by Schienert & Shalk; Bernhard–Nocht–Inst. Of Tropical Medicine, Virology Dept., Hamburg, DE; Eppendorf products, application catalogue from *http://www.eppendorf.com*.

Zeng et al. (1994) Nucl. Acids Res. 22: 4381–4385.

Coche (1997) Methods Mol. Biol. 67: 359–369.

Coche (1997) Methods Mol. Biol. 1997; 67: 371–87.

Diachenko et al. (1999) Met. Enzymol. 303: 349–380.

* cited by examiner

*Primary Examiner*—Carla J. Myers
(74) *Attorney, Agent, or Firm*—Browdy and Neimark, PLLC

(57) ABSTRACT

This invention provides methods for constructing a normalized cDNA library, constructing a low copy gene library, preparing a probe from a biological sample and a kit for constructing a normalized cDNA library.

15 Claims, 5 Drawing Sheets

SEQUENCE LISTING

```
<160> NUMBER OF SEQ ID NOS:   35

<210> SEQ ID NO 1
<211> LENGTH: 63
<212> TYPE: DNA
<213> ORGANISM: Artificial Organism
<220> FEATURE:
<221> NAME/KEY: misc_feature
<222> LOCATION: (1)..(35)
<223> OTHER INFORMATION: oligo dt primer, "v" is any nucleotide a,c or
      g but not t

<400> SEQUENCE: 1
tgcatggcac agtactgagt ggtatcgact cgtacaggcg cgccttttttt ttttttttttt     60 ttv                                                                    63

<210> SEQ ID NO 2
<211> LENGTH: 16
<212> TYPE: DNA
<213> ORGANISM: Artificial Sequence
<220> FEATURE:
<221> NAME/KEY: misc_feature
<222> LOCATION: (1)..(16)
<223> OTHER INFORMATION: killer primer

<400> SEQUENCE: 2
tgcggcacag agaaaa                                                      16

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 3
gaagagatga gtcctgagtc                                                  20
```

```
<210> SEQ ID NO 4
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: killer primer

<400> SEQUENCE: 4
gtgctctgtg tatgtggta                                              19

<210> SEQ ID NO 5
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 5
cacagcagtg aagacggaca                                             20

<210> SEQ ID NO 6
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: killer primer

<400> SEQUENCE: 6
ctgtactgta gccaatcaa                                              19

<210> SEQ ID NO 7
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 7
aaccgtcatt gattatggaa                                             20

<210> SEQ ID NO 8
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 8
attgaactgc aagagcaaga                                             20

<210> SEQ ID NO 9
<211> LENGTH: 20
<212> TYPE: DNA
<213> ORGANISM: Artificial Sequence
<220> FEATURE:
<221> NAME/KEY: misc_feature
<222> LOCATION: (1)..(20)
```

```
<223> OTHER INFORMATION: killer primer

<400> SEQUENCE: 9
gcggaatgat catgggtggg                                           20

<210> SEQ ID NO 10
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: killer primer

<400> SEQUENCE: 10
tgaatgaaat aaaggtggt                                            19

<210> SEQ ID NO 11
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: killer primer

<400> SEQUENCE: 11
ttcacggcat cttcccga                                             18

<210> SEQ ID NO 12
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 12
taactcagga atggatacac                                           20

<210> SEQ ID NO 13
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 13
acacaaggga tcataaattg                                           20

<210> SEQ ID NO 14
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 14
aggatcctca tcaatagata                                           20

<210> SEQ ID NO 15
<211> LENGTH: 20
```

```
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 15
acgtatagga atagtcaaac                                                        20

<210> SEQ ID NO 16
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 16
tcggagctgg ggaccgaacc                                                        20

<210> SEQ ID NO 17
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 17
cctaggtaag cgctctacca                                                        20

<210> SEQ ID NO 18
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: killer primer

<400> SEQUENCE: 18
tagaagctga tcagttttcg a                                                      21

<210> SEQ ID NO 19
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: killer primer

<400> SEQUENCE: 19
tagaggcact atttctagta c                                                      21

<210> SEQ ID NO 20
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: killer primer

<400> SEQUENCE: 20
```

```
tcaggtgcca atgaaaccca g                                              21
```

<210> SEQ ID NO 21
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: killer primer

<400> SEQUENCE: 21

```
tgcaccacag gaaatgtaga a                                              21
```

<210> SEQ ID NO 22
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 22

```
tgcagaagca tcaggccagg                                                20
```

<210> SEQ ID NO 23
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 23

```
ttaggaaggg gacccgatcc                                                20
```

<210> SEQ ID NO 24
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 24

```
tgaagaaatg gtacaaatta                                                20
```

<210> SEQ ID NO 25
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: killer primer

<400> SEQUENCE: 25

```
tggtgcaact tatagaaaag at                                             22
```

<210> SEQ ID NO 26
<211> LENGTH: 20
<212> TYPE: DNA
<213> ORGANISM: Artificial Sequence
<220> FEATURE:
<221> NAME/KEY: misc_feature

```
<222> LOCATION: (1)..(20)
<223> OTHER INFORMATION: killer primer

<400> SEQUENCE: 26
acatgtagtc agaaaacacg                                               20

<210> SEQ ID NO 27
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 27
tacagatcac ccaagaacat                                               20

<210> SEQ ID NO 28
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: killer primer

<400> SEQUENCE: 28
cgatgaccac attcagttat                                               20

<210> SEQ ID NO 29
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: killer primer

<400> SEQUENCE: 29
tcccatggga acatccctgg a                                             21

<210> SEQ ID NO 30
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: killer primer

<400> SEQUENCE: 30
ctgctgctgt gcctcttctc ta                                            22

<210> SEQ ID NO 31
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: killer primer

<400> SEQUENCE: 31
ccccggtaag tatgtttgtt a                                             21

<210> SEQ ID NO 32
```

```
<211> LENGTH: 45
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: Adapter Phosphate needed for ligation should
      be 5' Phgcaggtacgt c
<223> OTHER INFORMATION: gtaccgcgg ccgcgtacgt cgcctagtcg acctg 3

<400> SEQUENCE: 32
gcaggtacgt cgtaccgcgg ccgcgtacgt cgcctagtcg acctg                45

<210> SEQ ID NO 33
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: adapter

<400> SEQUENCE: 33
gcaggtacgt cgtaccgcgg ccttt                                      25

<210> SEQ ID NO 34
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 34
tcgatggcac agtactgagt                                            20

<210> SEQ ID NO 35
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer

<400> SEQUENCE: 35
caggtcgact aggcgacgta cgcg                                       24
```

SEQUENCE SPECIFIC AND SEQUENCE NON-SPECIFIC METHODS AND MATERIALS FOR CDNA NORMALIZATION AND SUBTRACTION

CROSS REFERENCE TO RELATED APPLICATIONS

Not applicable

STATEMENT REGARDING FEDERALLY SPONSORED RESEARCH AND DEVELOPMENT

Not applicable

INCORPORATION BY REFERENCE

Each of the applications and patents cited in this text, as well as each document or reference cited in each of these applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text; and, each of these documents or references ("herein-cited documents or references"), as well as each document or reference cited in each of the herein-cited documents or references (including any manufacturer's specifications, instructions, etc.), is hereby expressly incorporated herein by reference. Further, various references are cited by their WWW addresses and the content of these references are also expressly incorporated herein by reference.

FIELD OF THE INVENTION

The present invention discloses methods and materials that efficiently normalize cDNA libraries. The present invention also discloses methods and materials for aiding subtractive/differential hybridization and other normalization procedures. The methods and materials can be packaged in the form of a kit. The present invention supports a wide variety of genetic applications, including the isolation, identification and analysis of genes, the analysis and diagnosis of disease states, the study of cellular differentiation, and gene therapy.

BACKGROUND OF THE INVENTION

Approximately 20,000 genes are expressed in a typical mammalian tissue. However, not all genes are expressed in equal copy numbers. A wide range of gene expression patterns and/or levels are found among different cell types, or during stages of development.

Genes that are transcribed in many copies are categorized as "highly expressed genes" or "high copy number genes." High copy number genes are often associated with maintenance of basic cellular functions, and are therefore known as "house-keeping" genes. Transcription of house-keeping genes is usually constitutive.

Genes that are transcribed in fewer copies are categorized as "moderate or rarely expressed genes" or "medium or low copy number genes." Transcription of medium or low copy number genes is often subject to regulation, giving rise to differential patterns of expression. A regulated or restricted pattern of expression can be indicative of a unique gene function. For example, expression of VEGF, which plays a critical role in formation of the vascular endothelium, is restricted to the vascular endothelium. Mice that lack this gene have an embryonic lethal phenotype. De-regulation of differential gene expression is associated with many diseases, most notably, cancer.

Cloning of low copy number genes is difficult. Cloning involves screening of genetic libraries, such as cDNA or genomic libraries, using a polynucleotide complementary to the target gene. Prohibitive levels of background in many cDNA libraries lead to repetitive screening and/or sequencing of large numbers of clones. When cDNA libraries are used, hybridization and related screening procedures would be optimized by reducing the amount of high copy number genes or "background" in the library. Presently, there are significant problems with the techniques available for improving the efficiency of cDNA library screening.

For example, a rat liver cDNA library is dominated by fewer than fifty highly/moderately expressed genes, which in turn constitute nearly 50% of the cloned genes (http://www.ncbi.nlm.nih.gov/UniGene/lib.cgi?ORG=Rn&LID=31) and create a large "background" against which low copy number genes must be selected. Consequently, rarely expressed genes, which are often the focus of research efforts to isolate disease genes, are "buried" among the background.

"Normalization" procedures reduce the redundancy of highly expressed genes, or background, in cDNA libraries, thereby increasing the relative amount of transcripts represented by rarely expressed genes. Previous normalization procedures concern annealing opposite strands of nucleic acids. That is, the higher the concentration of a nucleic acid fragment, the higher the probability that it will anneal to its complementary fragment. Thus, annealing occurs more rapidly to a high copy number transcript than a low copy number transcript.

Soares et al. (1994) Proc. Natl. Acad. Sci. USA 91:9228-32 concerns such a procedure, where the unannealed, more rarely expressed single-stranded nucleic acid population is separated from the more highly expressed double-stranded population. The separation method involves hydroxyapatite column chromatography, wherein the double-stranded DNA selectively binds to hydroxyapatite. The single-stranded DNA is recovered from the flow-through fraction, processed and cloned in bacteria. Despite claims of high "normalization efficiency", this method is cumbersome to use, requires high amounts of input DNA, involves several reaction steps, and results in a loss of material from failure to fully elute single-stranded DNA from the column. The end result is an incomplete reduction of genetic redundancy (or poor normalization). http://www.ncbi.nlm.nih.gov/dbEST/index.html provides public cDNA libraries.

Another normalization method concerns digestion by restriction endonucleases, wherein the preferential target is double-stranded DNA. This method is disclosed in "Normalizing cDNA libraries using the Eppendorf Thermomixer" by Scheinert & Schalk; Bernhard-Nocht-Inst. of Tropical Medicine, Virology Dept., Hamburg, Del.; Eppendorf products, application catalogue and http://www.eppendorf.com/prepa/page8.html.

Another method is enzymatic degrading subtraction (EDS) for construction of subtractive libraries from PCR amplified cDNA. Zeng et al. (1994) Nucl. Acids Res.

22:4381–4385. The tester DNA is blocked by thionucleotide incorporation, the rate of hybridization is accelerated by phenol-emulsion reassociation, and the driver cDNA and double-stranded hybrid molecules are enzymatically removed by digestion with exonucleases III and VII rather than by physical partitioning. Here, double-stranded DNA represents the more highly expressed genes, having a higher probability for annealing to its complementary fragment. EDS has been used to construct a substance library enriched for cDNAs expressed in adult but not embryonic rat brains.

Yet another normalization method involves hybridization to genomic DNA coated onto beads. In genomic DNA, all genes are essentially present in the same copy number, and thus highly expressed genes will hybridize to genomic DNA in the same copy number as rarely expressed genes. Coche (1997) Met. Mol. Biol. 67:359–369. However, this method suffers from many of the same shortcomings as hydroxyapatite-column-chromatography separation methods discussed above. Consequently, this method is not widely used for normalization, but for selecting cDNA encoded by a chromosome or genomic DNA fragment of interest.

Suppression Subtractive Hybridization (SSH) and other subtraction methods preserve the copy number difference in the subtracted population leading to redundancy. A modified SSH method was developed by Diachenko et al. (1999) Met. Enzymol. 303:349–380. The modified SSH attempts normalization and subtraction in one reaction.

In the end, hybridization-based methods that depend on the efficiency of hybridization and the sensitivity of the separation/selection techniques, are affected by or influenced by variability in sources of RNA, and thus lack reproducibility in practice. Moreover, current normalization methods are not recommended for full-length library preparation because they either require high temperature treatment to denature and renature the DNAs, which break longer DNA strands, or polymerase chain reaction (PCR) which preferentially amplifies shorter fragments. Genetic research requires better solutions to the problem of redundancy in cDNA libraries.

SUMMARY OF THE INVENTION

The present invention discloses novel methods and materials for normalizing nucleic-acid material. These methods and materials are based on a technique called "prime and kill." Unlike previous methods, prime and kill based methods or procedures act by preventing cDNA synthesis either by physical blockage or by cleavage of the RNA. The invention comprises two modes, the "Killer Primer mode" and the "conventional mode."

The killing reaction in Killer Primer mode involves the formation of RNA-DNA duplexes. The RNA is mRNA encoding the target and non-target genes, the DNA oligonucleotides are of preselected sequences, complementary to the 3' end of target RNA transcripts of highly and/or moderately expressed genes. Once the duplexes are formed, the hybridized RNA is specifically cleaved by RNAse H. The result is that the target RNA is cleaved into a 3'-end poly-A mRNA strand, and usually just one other, longer fragment. Double-stranded cDNA is then synthesized, from an oligo(dT) primer, complementary to the poly-A mRNA sequence, and containing a first upstream restriction endonuclease site, preferably an AscI site, which is useful for subsequently specifically cloning non-target genes. Adapters with a second restriction endonuclease site are then ligated to both ends of all the cDNA molecules. The cDNAs are then digested with both first and second restriction endonucleases and ligated into a suitable vector having corresponding restriction endonuclease sites.

The Killer Primer mode has the following steps. Highly and/or moderately expressed genes ("target genes") are selected by known expression patterns (such as expressed sequence tag ("EST") databases) in the tissue of interest, or by constructing a mini cDNA library and sequencing a random selection of, for instance, about 500 clones, or both. "Killer Primers" are then designed and synthesized. These Killer Primers are oligonucleotides complementary to the 3' ends of the mRNA encoding the target genes ("target mRNA"). The mRNA is exposed to an excess of Killer Primers under conditions sufficient to form heteroduplexes specifically with the Killer Primers and the target mRNA. A killing reaction is then performed where RNAse H creates sequence-specific nicks in the heteroduplexed target mRNA.

First and second strand cDNA synthesis is then performed by reverse transcription of the mRNA. Non-target mRNA is specifically primed with oligo(dT) primers containing a first restriction endonuclease recognition site. Optionally, tests are performed to test the efficiency of killing and "cross-killing" (i.e. killer-primer priming of cDNA synthesis on non-target mRNA) by PCR. The cDNA is then ligated to adapters containing a second restriction endonuclease site (EcoRI or NotI are preferred restriction endonucleases). The ligation products are size-fractionated to remove fragments corresponding to 3' ends of target cDNA. cDNAs are digested with the first and second restriction endonucleases and specifically cloned into a vector appropriately digested with the first and second restriction endonucleases.

The Killer Primer mode of the method allows specific cloning of the non-target cDNA exclusively, while the target genes will not get inserted into the plasmid because they lack the first restriction endonuclease site and therefore are flanked by only the second restriction endonuclease site. Thus only the non-target cDNA is cloned.

In another embodiment, the invention involves the following steps. Synthesizing short first strand cDNA extensions on RNA of interest using random primers or oligo(dT) primers or anchored oligo(dT) primers. Digesting the RNA molecules and purifying short first strand cDNA. Mixing the purified first strand cDNA with the same RNA source (for normalization) or mixing the purified first strand cDNA with a different RNA source of interest (for subtraction). Adding RNAse H to the mixture of steps obtained and incubating the mixture at a suitable temperature such as 37° C. or 42° C. Denaturing the DNA-RNA duplex at a suitable temperature, preferably 70° C.; optionally repeating the process steps of incubation and denaturation without adding RNAse H in each cycle; and synthesizing cDNA using standard methods, followed by cloning. In one preferred embodiment, the RNAse H is an *E. coli* RNAse H. In another preferred embodiment, the RNAse H is a thermostable RNAse H such as Hybridase™.

This embodiment, when used for normalization, allows preferential elimination of highly expressed genes through cycling of the killing reaction. Thus, the lower the copy number of the mRNA, the more frequently it will be cloned. When used for subtraction, this embodiment allows enrichment of differentially expressed genes by degrading other mRNAs through killing reactions.

It is noted that in this disclosure, terms such as "comprises", "comprised", "comprising" and the like can have the meaning attributed to it in U.S. Patent law; e.g., they can mean "includes", "included", "including" and the like. These and other embodiments are disclosed or encompassed by the following.

DETAILED DESCRIPTION OF THE INVENTION

Figure 1A:
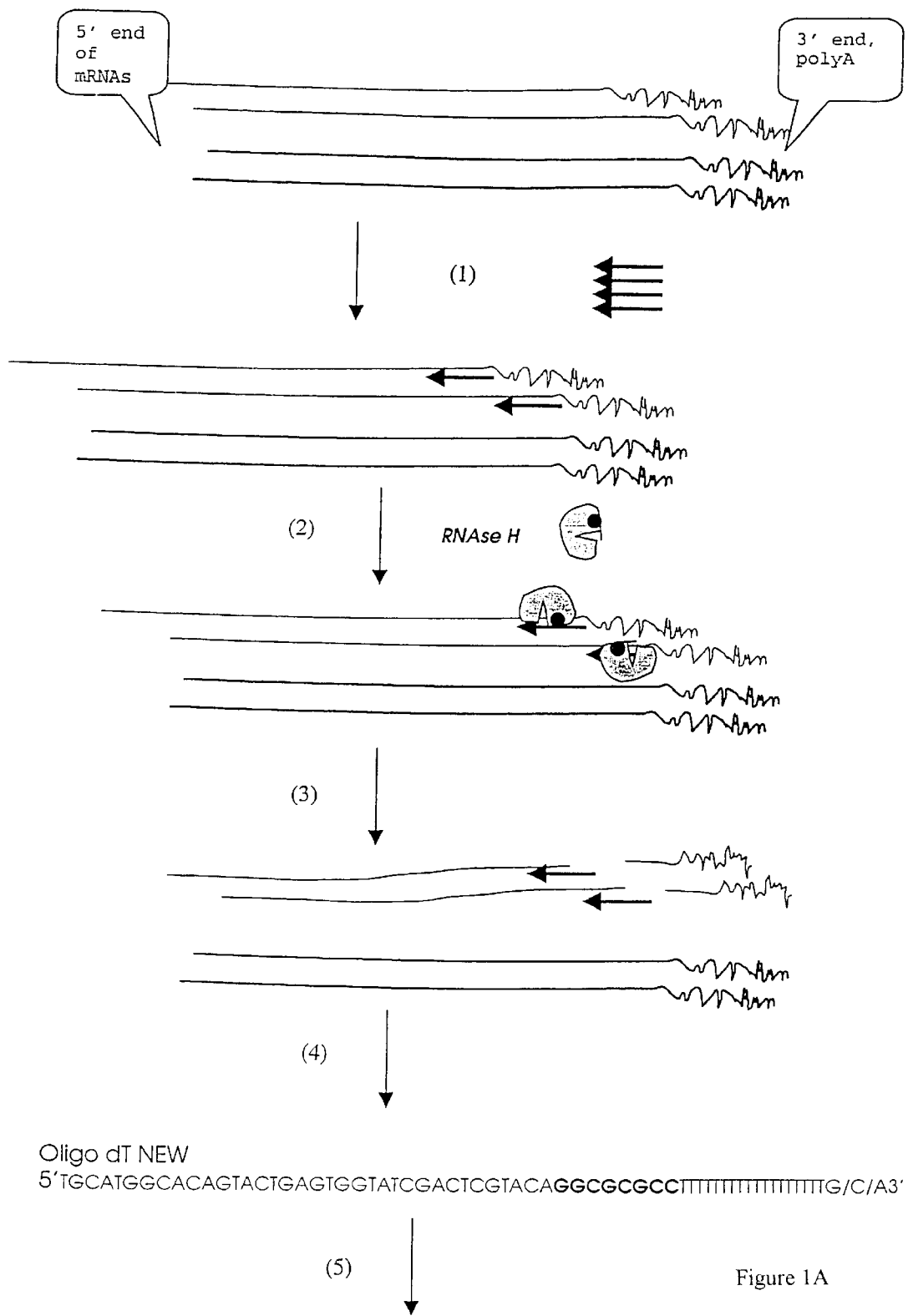
FIG. 1 shows the Killer Primer mode of the prime and kill method.
  (1) Annealing of the targeted RNAs to excess amount of 20 to 25 base-long Killer Primers; The thin lines represent targeted RNAs and the thick lines represent non-targeted RNAs;
  (2) The Killer Primers are represented by the arrows and are made to target sequence close to polyA of high copy genes;
  (3) Adding RNAse H to the solution wherein the RNAse H specifically cleaves the RNA strand of DNA-RNA hybrids;
  (4) Breaking the targeted RNAs near the polyA (note that RT can extend Killer Primers on the target RNAs because the target RNA is cleaved predominantly at the 5' side of the Killer Primer;
  (5) Denaturing RNAse H by heat and synthesizing first strand cDNA with oligo dT new primer (SEQ ID NO:1) in the same tube using standard protocols (the efficiency of killing and the frequency of cross killing can be studied on first strand cDNA by PCR with forward and reverse primers);
  (6) Synthesizing second strand in the same tube, checking ds cDNA on gel, purifying ds cDNA and ligating EcoRI sticky end adapters (the PCR primer sites are near the 5' end and the GGCGCGCC that is adjacent to the polyT represents AscI site);
  (7) After EcoRI adapter ligation, the types of fragments present in the cDNA preparation are shown as follows;
  (8) Treating the cDNA preparation with Kinase (to phosphorylate EcoRI ends), digesting with AscI, running on gel and cutting gel slice with fragments above 300 base pairs. The eluted fragments of more than 300 base pairs are ligated to dephosphorylated pQ which is digested with EcoRI-AscI and then the pQ is transformed to *E. coli.* competent cells and plated on LB Amp plates. The fragments from targeted RNAs contain EcoRI on both ends and thus will not be cloned. Fragments that are less than 150 base pairs are removed in the gel;
  (9) 3' side of targeted RNAs size: from 36 bp to 150 bp depending on the site targeted by Killer Primers; and
  (10) All cDNAs at 3' side have 70 bases.
Figure 1B:
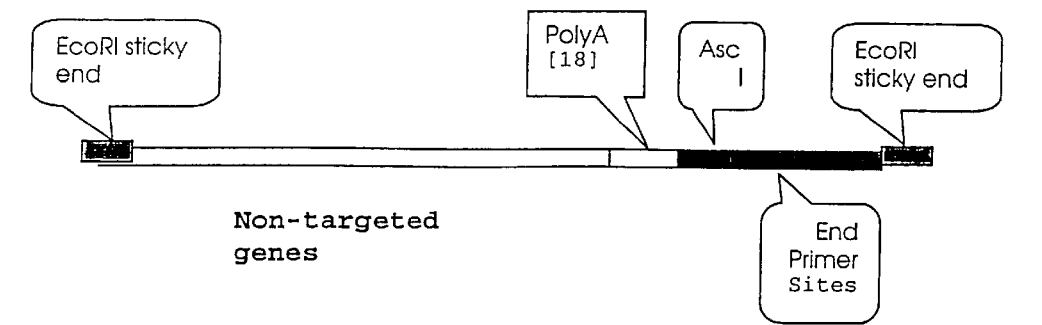
Figure 1B:
Figure 1B:
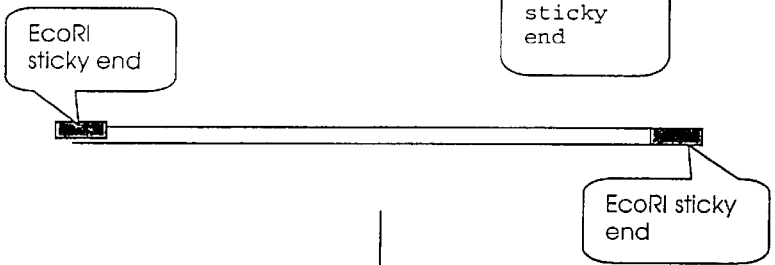
Figure 1B:
Figure 1B:
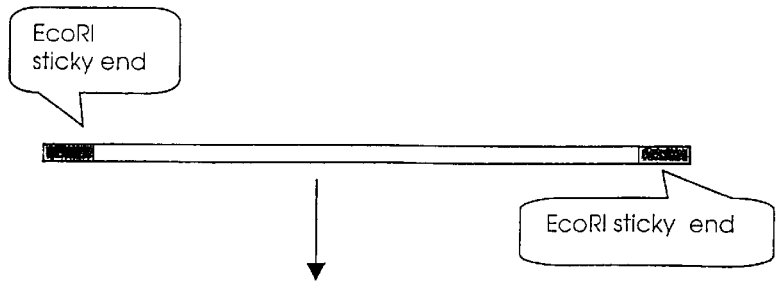
Figure 1C:
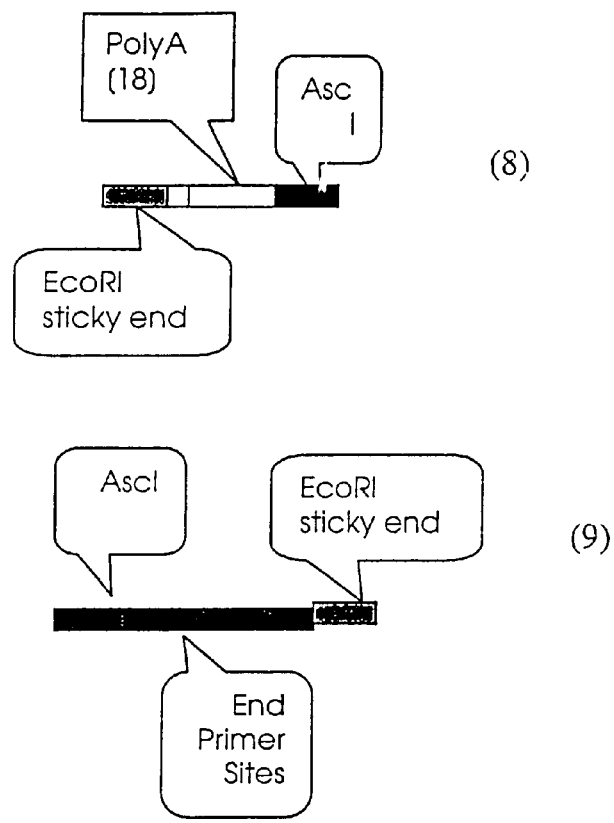

One object is providing methods and materials for obtaining nucleic acid material enriched for cDNA of rarely expressed genes. Another object is providing methods and materials for obtaining nucleic acid material enriched for cDNA of differentially expressed genes amongst two RNA sources.

Another object is obtaining nucleic acid material enriched for cDNA of rarely expressed genes by targeting and eliminating cDNA of some or all highly and/or moderately expressed genes (target genes). In one embodiment, the target genes comprise about 0.5 to 90 percent of all the genes in the sample. In another embodiment, the target genes comprise 1 to 50 percent of all the genes in the sample. In a preferred embodiment, the target genes comprise 1.5 to 20 percent of all the genes in the sample.

Yet another object is obtaining nucleic acid material enriched for cDNA of rarely expressed genes by selectively amplifying the corresponding cDNA. A further object is obtaining nucleic acid material enriched for cDNA of rarely expressed genes by both targeting and eliminating cDNA of some or all highly and/or moderately expressed genes, and by selectively amplifying cDNA only of rarely expressed genes. A further object is obtaining a cDNA library enriched for cDNA of rarely expressed genes. Another object is a kit for obtaining nucleic acid material and/or a cDNA library enriched for cDNA of rarely expressed genes. Another objects to aid or enhance normalization or subtractive/differential hybridization procedures. Another object is to prepare a probe molecule by performing a reverse transcription reaction following the killing reaction.

The present invention provides novel methods and techniques for normalizing a cDNA library, by forming RNA-DNA duplexes from DNA oligonucleotides of preselected sequences, complementary to the 3' end of RNA transcripts of highly and/or moderately expressed genes, and applying RNase H to exclusively cleave such RNA-DNA duplexes into a 3'-end poly-A mRNA strand, and, usually, one other, longer mRNA fragment. Double-stranded cDNA is then synthesized. The first strand can be primed by the cleaved heteroduplex, as well as by the addition of a oligo(dT)-containing primer that anneals to the poly-A sequence on non-target mRNA. The oligo(dT) primer contains a first restriction endonuclease site.

Adapters containing a second restriction endonuclease site, are then ligated to both ends of all the cDNA molecules. Gel electrophoresis separates out the cDNA gene fragments shorter than 150 bp, corresponding at the cDNA primed by the 3'-end poly-A mRNA strand of the target, cleaved mRNA transcript. Digestion with the first restriction endonuclease leaves the target cDNA fragments with the second restriction endonuclease site at both ends. In the conventional mode, there is no need to design chemically synthesized Killer Primers and therefore, this is more efficient and cost-effective than the Killer Primer mode. The other advantage of the conventional mode is that normalizations on mixed pool of tissues and mRNA of unstudied sources can be performed. One main disadvantage is that the conventional mode requires more mRNA, or total RNA for short primer synthesis. However, this can be overcome by cycling of the killer reaction. In one embodiment, oligo dU primers can be used to replace the dT primers. In addition, a variant of oligo dT or oligo dU primers is created when one or more T or U of the dT and dU primers are substituted by one or more of C, G, or A.

The cDNA encoding non-target genes can then be selectively inserted, as a function of the first and second restriction endonuclease sites, into vectors having a first restriction endonuclease cohesive end and a second, different, restriction endonuclease cohesive end. The present invention thus produces cDNA libraries that are selected for non-target genes, from which target highly and/or moderately expressed genes have been eliminated.

The methods and materials provided herein efficiently reduce the redundancy of highly expressed genes, and increase the relative amount of transcripts of rarely expressed genes. While conventional normalization methods depend on finely tuned hybridization kinetics, the prime and kill technique depends on saturation hybridization wherein high or saturating concentrations of "killer" primers complementary to target mRNA transcripts of highly and/or moderately expressed genes, are used.

"High copy genes" or "highly expressed genes" means the mRNAs encoding these genes equal or exceed 0.5% of the mRNA population transcribed from all the active genes in a tissue. "Low copy genes" or "rarely expressed genes" means mRNAs transcribed from these genes are equal to or below 0.0001% the mRNAs transcribed from all the active genes in a tissue.

The terms "hybridizes" and "hybridizing" relate to stringent conditions as, inter alia, defined herein above, e.g. 0.2×SSC, 0.1% SDS at 65° C. Said conditions comprise hybridization as well as washing conditions. However, it is preferred that washing conditions are more stringent than hybridization conditions. By setting the conditions for hybridization, a person skilled in the art can determine if strictly complementary sequences or sequences with a higher or lower degree of homology are to be detected. The choice of conditions is within the skill of one in the art. Such conditions can be determined according to protocols described, for example, in Sambrook, Molecular Cloning, A Laboratory Manual, $2^{nd}$ edition (1989), Cold Spring Harbor Laboratory Press, Cold Spring Harbor, N.Y. or Hames and Higgins, "Nucleic acid hybridization, a practical approach", IRL Press, Oxford (1985). Non-stringent hybridization conditions for the detection of homologous and partially complementary sequences can be set at 6×SSC, 1% SDS at 65° C.

"DNA" includes, but is not limited to, cDNA as well as genomic DNA. Furthermore, the nucleic acid molecules can also be a RNA molecule such as mRNA. "Nucleic acid molecule" comprises also any feasible derivative of a nucleic acid to which a nucleic acid probe can hybridize. The nucleic acid probe itself can be a derivative of a nucleic acid molecule capable of hybridizing to the nucleic acid molecule or the derivative thereof. The term "nucleic acid molecule" further includes peptide nucleic acids (PNAs) containing DNA analogs with amide backbone linkages. Nielson (1991) Science 254:1497–1500.

RNAse H selectively degrades the RNA strand of an RNA-DNA heteroduplex producing 5' phosphate-terminated oligoribonucleotides. RNAse H cleaves unwanted ("target") mRNA transcripts of highly and/or moderately expressed genes, duplexed with chemically or enzymatically synthesized DNA oligonucleotides ("Killer Primers"), preselected as complementary to sequences at the 3' ends of the target mRNA transcripts.

RNAse H1 catalyzes the formation, as well as cleavage, of RNA/DNA hybrids of stable DNA hairpin or duplex oligomers. Li et al. (1998) Biochem. 37:5154–5161. A 15 bp target sequence was selected from within a 79 bp RNA transcript, complementary DNA sequences were designed, including seven, single-stranded, 10–15 bp DNA oligos, a 10 bp DNA duplex, and five, hairpin DNA oligos, each having a 10 bp stem and 15 bp loop. DNA sequences complementary to the RNA target site were located in a region spanning the loop and 3' side of the stem or the hairpin DNAs. RNA/DNA hybrid formation was analyzed by gel electrophoresis mobility shift assay ("gel-shift assay"). RNA titration of a 15 bp, $^{32}$P-labeled DNA oligo produced a band shift upward, indicating formation of the RNA/DNA complex. By contrast, no RNA/DNA complex was detected when the most stable (Tm=71° C.) hairpin DNA was combined with excess RNA. The least stable hairpin DNA (Tm=62° C.) formed a slight (approximately 8%) hybrid.

Although no RNA/DNA hybrid was expected from thermodynamic calculations, an RNAse H assay at 25° C. showed that either hairpin or duplex DNA, having a 10 bp complementary sequence, enables RNA cleavage. Thus, RNAse H catalyzed hybrid formation and cleavage can occur at temperatures well below their Tm.

The application of standard cloning procedures, including, but not limited to, gel electrophoresis, restriction endonuclease digestion, RNAse H digestion, polymerase chain reaction, reverse transcription, DNA extraction and/or precipitation, are well known to one of skill in the art of molecular biology. For example, properties and uses of RNAse H have been described. Hogrefe et al. (1990) J. Biol. Chem. 265:5561–6; Uchiyama et al. (1994) J. Mol. Biol. 243:782–91; Boiziau et al. (1992) Proc. Natl. Acad. Sci. USA 89:768–72; Lima et al. (1992) Biochem. 36:390–398; Porter et al. (1997) Anal. Biochem. 247:279–286; Giles et al. (1992) Nucl. Acids Res. 20:763–770 and Giles et al. (1998) Biochem. 37:5154–61. Restriction endonucleases are well known in the art and are not described in detail herein. For use in the invention, the restriction endonuclease preferably recognizes an 8 bp site but some rare restriction endonucleases recognizing a 6 bp site and even a 4 bp site could also be used. Preferably, the first and second restriction endonucleases do not recognize the same site.

Following RNAse H treatment, target mRNA of the RNA-DNA duplexes is degraded at the 3' end, near the poly-A region, creating two strands of mRNA, a 3'-end poly-A mRNA strand of 36 to 150 bp and usually just one other, longer target mRNA strand upstream of the cut. First-strand cDNA is then synthesized, primed by the oligo (dT) primers still associated with the target RNA, as well as by added oligo(dT) primers that contain a first restriction endonuclease recognition site and, optionally, a PCR primer site. Second-strand cDNA is then synthesized. Adapters containing a second restriction endonuclease site are then ligated to all of the cDNA molecules. Gel electrophoresis is used to size-fractionate the DNA, separating out fragments less than 150 bp long, i.e. double-stranded cDNA corresponding to the short 3'-end poly-A target-mRNA strand. Then first restriction endonuclease is used to remove the oligo(dT) end of the non-target cDNA of rarely expressed genes, producing cDNA molecules with one ligated second restriction endonuclease cohesive end, and one first restriction endonuclease cohesive end. The remaining, target, cDNA molecules, corresponding to the longer target mRNA, have a second restriction endonuclease site at both ends.

Next, a cDNA library is made with vectors prepared to have a first restriction endonuclease cohesive end and a second restriction endonuclease cohesive end. Only cDNA of non-target genes is inserted into the vectors and cloned. Gel separation and failure to insert into cloning vectors eliminates, or "kills" target genes. The method thus produces cDNA libraries selected for non-target genes, from which target highly and/or moderately expressed genes have been substantially eliminated.

The molecules hybridizing to the nucleic acid molecules also include fragments, derivatives and allelic variants of the above-described nucleic acid molecules that encode polypeptides. In this regard, fragments are defined as parts of the nucleic acid molecules, which are long enough to encode the polypeptides. The term derivatives means that the sequences of these hybridizing molecules differ from the sequences of the above-mentioned nucleic acid molecules at one or more positions and that they exhibit a high degree of homology to these sequences. Homology means a sequence identity of at least 35%, in particular an identity of at least 45%, preferably of more than 50%, more preferably more than 60%, more preferably more than 70%, more preferably more than 80% and still more preferably a sequence identity of more than 90%. The person skilled in the art can employ computer programs and packages in order to determine homology values. Generally, nucleotide or amino acid sequence identities/homologies can be determined conventionally by using known computer programs such as BLASTN, BLASTP, NALIGN, PALIGN or bl2seq using particular algorithms to find the best segment of homology between two segments. The comparative analysis of the percentage of identities at the amino acid level are preferably obtained using the "bl2seq" program from NCBI using the following parameters: Open Gap Cost: 11 and Gap Extension Cost:1. The program allows any positive integer for the value(s).

Different (but similar) PCR conditions can be employed to amplify the non-target cDNA. For example, the person skilled in the art can modify denaturing, annealing- and or extension-times and temperatures. Said modifications can be, inter alia, in the range of 0.2 to 0.5 min in the extension time. Modifications in the temperature can involve +/−3° C. in the denaturing step, +/−5° C. in the annealing step and +/−3° C. in the extension step. The person skilled in the art knows that modifications depend on a variety of factors which comprise, inter alia, buffer constitution, buffer concentration, DNA and/or enzyme concentrations, purities, PCR equipment, etc.

The invention further provides a method for constructing a normalized cDNA library. The method involves selecting and synthesizing DNA oligonucleotides having sequences complementary to sequences at the 3' poly-A end of mRNA transcripts of target genes that are high copy genes in a biological sample. The resulting oligonucleotides are then annealed to the RNA of interest to produce RNA-DNA heteroduplexes that are specifically cleaved with an RNAse H. cDNA is then synthesized by reverse transcription primed by both the cleaved RNA-DNA heteroduplex and added oligo(dT) primers containing sequences for both a constant PCR primer site and a first restriction endonuclease recognition site. The second-strand cDNA is then synthesized, producing double-stranded cDNA molecules. Adapters are then ligated to both ends of the cDNA. The adaptors have cohesive ends of a second restriction endonuclease site. Double-stranded cDNA fragments less than 150 bp long corresponding to the 3'-end poly-A mRNA strand are removed from the reaction mix and the remaining double-stranded cDNA molecules are digested with the first restriction endonuclease. In the case of non-target cDNA, this removes the oligo(dT)-primed end. Restriction endonuclease digestion with the second restriction endonuclease cleaves one end of the non-target cDNA and both ends of the target cDNA. A cDNA library is then constructed using vectors prepared to have one cohesive end produced by the first restriction endonuclease and one cohesive end produced by the second cohesive enzyme, thereby incorporating only double-stranded cDNA of non-target expressed genes, and excluding double-stranded DNA of target, highly expressed genes.

In one embodiment, the DNA oligonucleotides used for forming the DNA/RNA heteroduplex are attached to solid support or biotinylated. "Solid support material" includes, but is not limited to membranes, chips, pins, beads, plates, filters, resins, etc. The solid support material can include, but is not limited to, nylon; nitrocellulose; chromatographic bed materials; monodisperse latex particles, including those based on styrene, chemically-modified styrene, propylene, methacrylate, butadiene, acrylonitrile or other monomers; polyglutaraldehyde microspheres (e.g., as manufactured by Polysciences, Inc.); nylon beads; chemically-modified nylon beads; oxirane acrylic beads such as Eupergit™ (Rohm Pharma, Darmstadt, W. Germany); copolymers of acrylic ester; and acrylic amide. Methods of binding DNA primers to these materials include the following: DNA primers can be covalently bound to an activated chromatographic resin having reactive groups capable of forming covalent bonds with proteins, such as CNBr-activated Sepharose-4B, CNBr-activated 4% agarose or CNBr-activated Sepharose-6MB (Pharmacia P-L Biochemicals; Piscataway, N.J.), or other resin, such as cellulose, by conventional means. DNA primers can be bound to polystyrene beads by non-specific adsorption. DNA primers can also be bound covalently to polystyrene beads containing carboxyl or amino functional groups (Polysciences, Inc., Warrington, Pa.) by conventional means. The DNA primers can be bound non-diffusively to a solid support, either absorptively or covalently, either directly or through a linker molecule. U.S. Pat. No. 4,963, 658. In another embodiment, the solid support comprises a membrane, a chip, a pin, a bead, a plate, a filter, or a resin.

In another embodiment, the RNAse H is from a bacterium, a plant or an animal. In another embodiment, the bacteria comprise *E. coli*. In another embodiment, the RNAse H is a thermostable RNAse H. Preferably, the first restriction endonuclease comprises AscI. Preferably, the second restriction endonuclease is EcoRI or NotI.

Restriction endonucleases include, but are not limited to, AatII, AccI, Bshl236I, AccIII, HinII, DraI, AluI, Bsu36I, ApaI, ApaLI, AvaI, AvaII, NsiI, BamHI, BanI, BclI, BglI, BglII, Bpu1102I, Bsh1236I, BsmI, Bsh1236I, Bsp106I, BspCI, BssHII, BstNI, BstXI, Bsu36I, CspI, DdeI, DpnI, DraI, EcoO109I, DraIII, Eam1104I, EcoO109I, Eco47III, Xma, Eco72I, EcoRI, EcoRII, EcoRV, Bpu1102I, HaeII, PalI, HindII, HindIII, HinfI, HinII, HpaI, HpaII, KpnI, SacII, MboI, MluI, MnlI, MspI, Bsu36I, MunI, NaeI, NarI, NciI, NcoI, NdeI, NheI, NotI, NruI, NsiI, PalI, PspAI, PstI, PvuI, PvuII, RsaI, SacI, SacII, SalI, Bsu36I, Sau3AI, SanDI, ScaI, SfiI, SmaI, SnaBI, SpeI, SphI, SrfI, SspI, StuI, StyI, TaqI, VspI, XbaI, XhoI, XhoII, PspAI and XmnI.

In another embodiment, the 3'-end poly-A mRNA strand is between about 0 and 150 bp. In another embodiment, the double-stranded cDNA fragments are size fractionated by gel electrophoresis.

In yet another embodiment, the oligonucleotides used to form the DNA/RNA heteroduplex have SEQ ID NO:31, to SEQ ID NO:30. The oligonucleotides of SEQ ID NOS: 2–31 are encompassed by the invention.

In another embodiment of the invention, the cDNA library preferentially contains clones encoding rarely expressed genes. In another embodiment, the rarely expressed genes are obtained by targeting and eliminating high copy genes. In another embodiment of invention, the rarely expressed genes are obtained by selectively amplifying cDNA of rarely expressed genes. In another embodiment, the rarely expressed genes are obtained by both targeting and eliminating cDNA of high copy genes and by selectively amplifying cDNA of rarely expressed genes.

In another embodiment, the biological sample is from an animal, a plant, a bacterium or a virus. The animal can be any suitable animal, including, but not limited to, a human, a dog, a pig, a goat, a sheep, a rabbit, a mouse, a rat, a zebrafish or a cow. Biological samples can be from any prokaryotic or eukaryotic cell. Suitable prokaryotic cells are those generally used for cloning like *E. coli* or *Bacillus subtilis*. Furthermore, eukaryotic cells comprise, for example, fungal or animal cells. Examples for suitable fungal cells are yeast cells, preferably those of the genus Saccharomyces and most preferably those of the species *Saccharomyces cerevisiae*. Suitable animal cells are, for instance, insect cells, vertebrate cells, preferably mammalian cells, such as e.g. CHO, Hela, NIH3T3, MOLT-4, Jurkat, K562, HepG2, 3T3-L1 (and derivatives thereof), HIB-1B, HEK 293, PAZ6. Villena (1998) Biochem. J. 331:121–127); and Strobel (1999) Diabetologia 42:527–533. Further suitable cell lines known in the art are obtainable from cell line depositories, like the American Type Culture Collection (ATCC).

This invention also provides a method for constructing a low copy gene library by a less direct method. Short first strand DNA extensions are made on a first RNA primed by random primers or oligo(dT) primers or anchored oligo(dT) primers. This DNA is then annealed with a 3' poly-A end of the RNA of interest. The RNA molecules are cleaved and the short first strand cDNA is purified. The short first strand cDNAs are mixed with a second RNA under conditions suitable to form heteroduplexes and RNAse H is added. Preferably, incubation is at a temperature of between 25° C. and 50° C. to cleave the cDNA-RNA duplex. The cDNA-RNA is then cleaved, preferably at a temperature between 60° C. and 90° C. Optionally these steps can be repeated after thermal denaturation of the DNA-RNA duplex. cDNA is then synthesized and cloned into a suitable vector. In a further embodiment, the vector is a pQ vector.

In one embodiment, the first RNA is from the same source as that of the second RNA for normalization. In another embodiment, the first RNA is from a different source than that of the second RNA for subtraction, In another embodiment, the thermal denaturation temperature of the DNA/RNA heteroduplex is between about 65° C. and 75° C. In yet another embodiment, the thermal denaturation temperature is 70° C.

The present invention further provides a kit for constructing a normalized cDNA library, containing an oligo(dT) primer, a buffer for synthesizing first strand cDNA, a killing reaction buffer and an RNAse H.

In another embodiment, the kit contains a DTT solution; an RNAse inhibitor; a dNTP solution; DNAse-free and RNAse-free water; reverse transcriptase; one or more ligation adaptors; one or more PCR primers; a product description and protocol.

Buffer and buffer solution means an aqueous solution having the ability to resist a change of pH on adding acid or alkali, or on dilution with water. Characteristic of a buffer solution is the presence of either of a weak acid and a salt of the weak acid, or a weak base and a salt of the weak base. Examples of buffer systems include, but are not limited to, acetic acid-sodium acetate, ammonium hydroxide-ammonium chloride, monobasic potassium phosphate-dibasic potassium phosphate, etc. A person skilled in the art knows various other buffers or buffer solutions that can be used, e.g. 10×universal buffer from STRATEGENE which comprises 1M KOAc, 250 mM Tris-Acetate (pH 7.6), 100 mM Mg(OAc)$_2$, 5 mM β-mercaptoethanol and 100 μg/ml BSA.

A solution is a homogeneous mixture that is prepared by dissolving a solid, liquid, or gas in another liquid and represents a group of preparations in which the molecules of the solute or dissolved substance are dispersed among those of the solvent. The solvent can be water or a buffer solution. Examples of solutions include, but are not limited to, dNTP solution in water or in buffer, DTT solution in water or in buffer, and RNAse H solution in water or in buffer, etc.

In another embodiment, the kit is for use in its Killer Primer mode, and contains computer software for selecting Killer Primers and for analyzing results, a control mRNA and Killer Primers for testing. In another embodiment, the kit is for use in its conventional mode, which further contains a thermal stable RNAse H.

The kits can be advantageously used, inter alia, for carrying out the method of producing a cDNA library and can be employed in a variety of applications referred to herein, e.g., as diagnostic kits, or as research tools. Additionally, the kit can contain means for detection suitable for scientific; medical and/or diagnostic purposes. The manufacture of the kits follows preferably standard procedures that are known to the person skilled in the art. Kits can advantageously include instructions for use and/or for admixture of ingredients.

The present invention also provides a method of preparing a probe from a biological sample by performing a killing reaction; and performing a reverse transcription reaction. In one embodiment of the method of preparing a probe, the reverse transcription reaction includes an oligo(dT) primer and a mix of deoxynucleotides. In another embodiment, the deoxynucleotides comprise Cy3-dCTP or Cy5-dCTP.

The invention further encompasses oligonucleotides having the sequences of SEQ ID NOS: 1–31. The oligonucleotides can have flanking sequences but are preferably not more than 100 nucleotides in length total. More preferably, the oligonucleotides are less than 50 nucleotides in length. Most preferably, the oligonucleotides have the sequences set forth in SEQ ID NOS: 1–31. The sequences can vary by a base or two that can reduce complementarity and thus decrease hybridization temperatures. Likewise, changes to the sequences can be made to account for allelic differences, thus increasing hybridization temperatures in a particular reaction.

The following examples illustrate but do not limit the invention.

EXAMPLE 1

The Killer Primer Mode

This example shows synthesis of a cDNA library of less than 25% redundancy. An overview of the Killer Primer mode is illustrated in FIG. 1. The first step in the Killer Primer mode is the identification of highly expressed genes using either the EST databases or by constructing a control cDNA library. The latter is preferred, because variations among RNA sources arising from differences in age, feeding, method of normalization and cloning can make extrapolation of database entries to copy numbers inaccurate.

The Killer Primer mode was tested on rat liver poly-A+ mRNA. Killer Primers corresponding to two abundant genes, the albumin gene and transferrin gene, were synthesized. The efficiency of killing and cross killing frequencies was tested and determined to work efficiently. Further studies were undertaken in which different lengths of Killer Primers, different annealing conditions and sources and concentrations of RNAse H were tested and optimized. An optimized protocol was determined to be:

1. PolyA + RNA (1–2 μg),
2. 5X first strand buffer (2 μl),
3. Killer Primer mix (or water as control) 10 pM/μl in ½X TE (1 μl)
4. DTT (1 μl),
5. RNAsin by Promega (1 μl),
6. Water to 9.5 μl Briefly, Killer Primers (20–25 bp) were annealed to target sequences located in close proximity to the polyA sequences of the high copy number genes. RNAse H was used to specifically cleave the RNA strands at the junction of the DNA-RNA duplex followed by heat inactivation of the RNAse H. All reactions were performed in one tube from start to finish. The reaction was carried out according to the following specifications:

1. 50° C. for 15 minutes
2. 37° C. for 5 minutes
3. Add 0.5 μl RNAse H
4. 37° C. for 30 minutes
5. 65° C. for 15 minutes (heat inactivation)
6. 42° C. for 5–10 minutes
7. Add 10 μl of oligo(dT) primer RT mix*
8. 42° C. for 1.5 hours
9. Chill tubes on ice and continue with second strand synthesis in the same tube

*Oligo(dT) primer RT mix for 2 tubes contains: oligo(dT) new primer, 10 pM/μl (2.5 μl); DTT (2.5 μl); RT buffer (5 μl); RNAsin (2.5 μl); dNTP (2.5 μl); Water (8.5 μl); and Superscript RT (1.5 μl).

The reaction was also carried out by incubating the cDNA-RNA duplex at 65° C. for 5 minutes and at 50° C. for 10 minutes and then at 37° C. RNAse H was then added and the mixture was incubated at 37° C. for 30 minutes. The targeted RNA was cleaved at a few base pairs within the binding regions of the Killer Primer.

Killer reaction took place in first strand buffer with the first 4 components. First strand buffer comprising 50 mM Tris-HCl (pH=8.3 at room temperature), 75 mM KCl, 3 mM $MgCl_2$, 10 mM DTT. The reaction also contained 0.5 mM each of dATP, dCTP, dTTP, dGTP, dNTP, 1–2 μg of mRNA (poly A+), 500 ng of oligo-dT primer, and 200 units of SuperScript reverse transcriptase.

Second Strand Synthesis

The protocol for this procedure was carried out according to the Clontech SSH Kit protocol. Briefly, while on ice, 80 μl of second strand mix with *E.coli* ligase, *E.coli* DNA Polymerase, and Boehringer Mannheim's/Pro's RNAse H was added to each sample. After five minutes, the samples were incubated at 16° C. for 1.5 hours. T4 DNA polymerase was added to each sample and incubated at 16° C. for 30 minutes and 37° C. for 30 minutes. Samples were purified through PCR purification columns (Qiagen) and eluted in 50 μl 0.5M TE. 1 μl of sample was run on an agarose gel to estimate the concentration.

Quality/Quantity Control

In order to check the killing efficiency, PCR was performed on samples of killed cDNA and control cDNA using the end primer and gene specific forward primer. In order to the check cross killing frequency of non-targeted, low copy number genes, PCR was carried out using gene specific forward and reverse primers for at least 6 non-targeted genes. Targeted high copy genes were not detected, while low to medium copy number genes showed no significant decrease in quantity.

Adapter Ligation Cloning

EcoRI adapters were ligated to cDNA a in 30–50 μl reaction volume consisting of 500 ng to 2 μg cDNA, ligase buffer and EcoRI sticky end adapters from Pro (1 μl if the volume is up to 30; 2 μl if the volume is 50 μl or more), at 16° C. over night with 800 units (2 μl) of NEB DNA ligase. Following heat inactivation of the ligase, T4 Kinase (2 μl) was added to the reaction, incubated at 37° C. for 30 minutes and heat inactivated at 65° C. for 30 minutes. NEB buffer 4 (10 μl), water (86 μl) and AscI (4 μl) were added and incubated at 37° C. for 3 hours. Samples were gel purified and fragments above 300 bp were eluted using QuiQuick gel extraction kit (Qiagen). Fragments were cloned into pQ AscI-EcoRI cut, dephosporylated and purified.

High efficiency *E. coli* competent cells were transformed and plated on LB ampicillin plates in the presence of X-gal and IPTG. PCR amplification of 100 colonies was performed to check for insert size. Positive clones were sequenced to check for redundancy, which was estimated to be less than 25%.

Control Library Preparation

Double stranded cDNA was prepared from total RNA, or preferably from polyA+RNA. When abundant genes were known within an RNA source, Killer Primers were included in the cDNA preparation. Eco RI adapters were ligated to cDNA in a reaction volume (20 μl) consisting of 100 ng to 250 μg cDNA, ligase buffer and EcoRI sticky end adapters from Pro (1 μl) at 16° C. overnight with 400 units of NEB DNA ligase (1 μl). DNA ligase was heat inactivated, and T4 Kinase (1 μl) was incubated at 37° C. for 30 min, followed by heat inactivation at 65° C. for 30 min. NEB buffer 4 (7.5 μl), water (66.5 μl) and AscI (2 μl) were added and incubated at 37° C. for 3 hours. Samples were gel purified and fragments above 300 bp were eluted using QuiQuick gel extraction kit (Qiagen). Fragments were cloned into pQ AscI-EcoRI cut, dephosporylated and purified.

High efficiency *E. coli* competent cells were transformed and plated on LB Amp plates in the presence of X-gal and IPTG. PCR amplification of 100 colonies was performed to check for insert size. Positive clones were sequenced to check for high copy number genes.

EXAMPLE 2

Identification of High Copy Genes and Synthesis of Killer Primers

The protocol in Example 1 was scaled up for use in normalizing cDNA library background from up to twenty abundant genes. Sixteen high copy number genes (constituting 35–40% redundancy in 'normalized' libraries) were identified based on data found at http://www.ncbi.nlm.nih.govlUniGene/lib.cgi?ORG=Rn&LID=31 and used for the construction of Killer Primers. Four additional high copy genes from a non-normalized cDNA library were also used. The sequences of the Killer Primers corresponding to high copy number genes in Rat liver tissue were as follows: (All sequences are in 5' to 3' direction)

| | | |
|---|---|---|
| AlbK2 | TGCGGCACAGAGAAAA | SEQ ID NO:2 |
| Alb K15 | GAAGAGATGAGTCCTGAGTC | SEQ ID NO:3 |
| TransK1 | GTGCTCTGTGTATGTGGTA | SEQ ID NO:4 |
| TransK2 | CACAGCAGTGAAGACGGACA | SEQ ID NO:5 |
| SelenoK1 | CTGTACTGTAGCCAATCAA | SEQ ID NO:6 |
| SelenoK2 | AACCGTCATTGATTATGGAA | SEQ ID NO:7 |
| Alpha2UK1 | ATTGAACTGCAAGAGCAAGA | SEQ ID NO:8 |
| Alpha2UK2 | GCGGAATGATCATGGGTGGG | SEQ ID NO:9 |
| TransytK1 | TGAATGAAATAAAGGTGGT | SEQ ID NO:10 |
| TransytK2 | TTCACGGCATCTTCCCGA | SEQ ID NO:11 |
| p450K1 | TAACTCAGGAATGGATACAC | SEQ ID NO:12 |
| p450K2 | ACACAAGGGATCATAAATTG | SEQ ID NO:13 |
| NGNGK1 | AGGATCCTCATCAATAGATA | SEQ ID NO:14 |
| NGNGK2 | ACGTATAGGAATAGTCAAAC | SEQ ID NO:15 |
| p450PB1K1 | TCGGAGCTGGGGACCGAACC | SEQ ID NO:16 |
| p450PB1K2 | CCTAGGTAAGCGCTCTACCA | SEQ ID NO:17 |
| ESTK1 | TAGAAGCTGATCAGTTTTCGA | SEQ ID NO:18 |
| ESTK2 | TAGAGGCACTATTTCTAGTAC | SEQ ID NO:19 |
| GLUTsK1 | TCAGGTGCCAATGAAACCCAG | SEQ ID NO:20 |
| GLUTsK2 | TGCACCACAGGAAATGTAGAA | SEQ ID NO:21 |
| ALPA1K1 | TGCAGAAGCATCAGGCCAGG | SEQ ID NO:22 |
| ALPA1K2 | TTAGGAAGGGACCCGATCC | SEQ ID NO:23 |
| FERRK1 | TGAAGAAATGGTACAAATTA | SEQ ID NO:24 |
| FERRK2 | TGGTGCAACTTATAGAAAAGAT | SEQ ID NO:25 |
| MITIF1k2 | ACATGTAGTCAGAAAACACG | SEQ ID NO:26 |
| MITIF1K1 | TACAGATCACCCAAGAACAT | SEQ ID NO:27 |
| HsULFOK1 | CGATGACCACATTCAGTTAT | SEQ ID NO:28 |
| HsULFOK2 | TCCCATGGGAACATCCCTGGA | SEQ ID NO:29 |
| AldoK1 | CTGCTGCTGTGCCTCTTCTCTA | SEQ ID NO:30 |
| AldoK2 | CCCCGGTAAGTATGTTTGTTA | SEQ ID NO:31 |

Testing Killing Efficiency

Of the 16 genes initially tested, 15 were killed efficiently and one, α-2-γ-globulin, was not killed efficiently. Possibly, the α-2-γ-globulin gene was not highly represented following the killing reaction. Testing the cross killing frequency of untargeted genes revealed a 40% improvement rate. Cross killing efficiency was calculated by amplifying non-targeted genes and comparing PCR results. The same conditions were used for library construction.

cDNA Synthesis and Cloning

Figure 2:
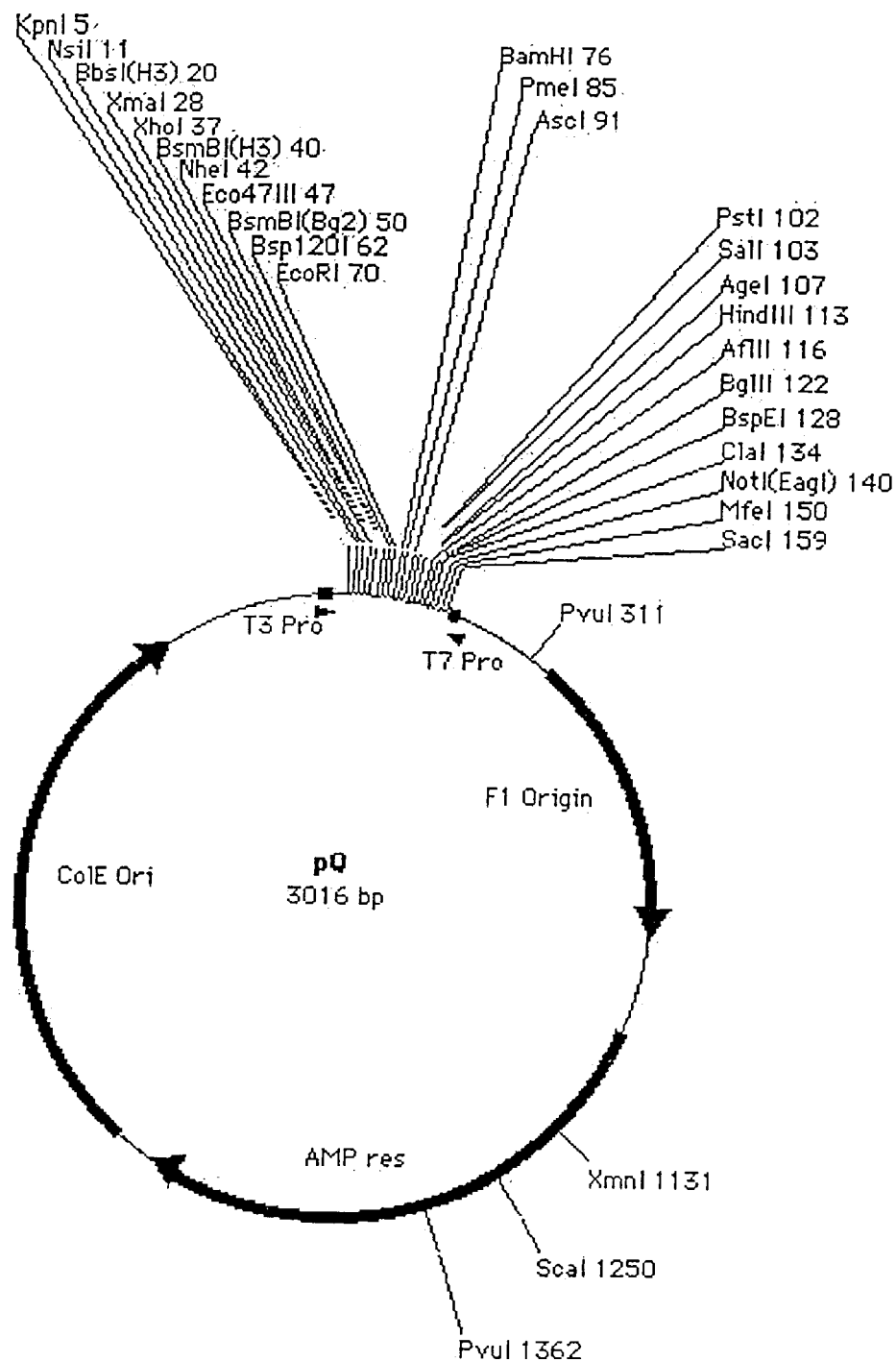
FIG. 2 describes the pQ vector having a plasmid size of 3016 bp.

First strand and second strand cDNA synthesis was carried out in the same tube following killing of the high copy number genes. A detailed protocol was described in Example 1. EcoRI cohesive-end adapters were ligated to the double-stranded cDNA and kinase. Following AscI digestion, samples were run on a 1% low melt agarose gel. Fragments above 200 bp were eluted and ligated to an AscI-EcoRI digested, dephosphorylated pQ plasmid. The dephosphorylated pQ vector was constructed as shown in FIG. 2. Colony PCR was done using T3–T7 primers and sequenced from the T3 end (EcoRI side) with dye terminators. Sequences were trimmed to remove flanking vector sequences and aligned using Vector NTI or Sequencher software and Blast searched in GenBank.

EXAMPLE 3

Construction of a cDNA Library from Rat Liver

To enhance the production of large libraries from the material obtained after the primer-induced killing reaction, the following procedures were introduced following the RNAse H killing reaction.

Double-stranded cDNA was purified over a TE400 column (Clontech) to remove small cDNA molecules produced as a result of RNAse H cleavage. Adapters were 5'PhG-CAGGTACGTCGTACCGCGGCCGCG-TACGTCGCCTAGTCGACCTG 3' (SEQ ID NO:32); and 3' CGTCCATGCAGCATGGCGCCGGAAA 5' (SEQ ID NO:33).

The Ph indicates phosphate group needed for the ligation. A 1:4 mix of the upper (SEQ ID NO:32) and lower (SEQ ID NO:33) oligonucleotides was annealed and used for ligation. The ligation reaction included 50 pmole of adaptor, 20 ng of cDNA and T4 DNA ligase combined under standard ligation conditions for blunt-end ligation reactions (7 hours at 8° C.).

The ligated material was amplified using a primer matching the oligo(dT) END region. 5' TCGATGGCACAGTACT-GAGT 3' (SEQ ID NO:34), and a second primer matching the ligated adaptor, 5' CAGGTCGACTAGGCGACG-TACGCG 3' (SEQ ID NO:35). PCR was carried out for 3 minutes at 94° C., followed by 25 cycles of 30 seconds at 94° C., 30 seconds at 58° C. and 3 minutes at 72° C. The reaction was ended by incubation at 72° C. for 7 minutes. The amplified material was digested with AscI (present in the oligo(dT) END sequence) and NotI (present in the adaptor sequence) and the digested material was separated on low melting agarose gel.

cDNA was eluted from either the 300 to 700 bp region or the 700 to 3000 bp region of the gel. Eluted fragments were ligated to an AscI-NotI predigested pQ plasmid. The ligation products were transformed in competent bacteria and plated on 10 cm LB amp plates. Clones were randomly chosen and PCR amplified.

In total, 45 clones from the control (untreated cDNA) and killed libraries were sequenced. Rat vitamin D binding protein mRNA and rat cytochrome P-450-LA-o were determined to represent more than 3% of the clones. Killer Primers for both the rat vitamin D binding protein mRNA and rat cytochrome P-450-LA-o were used for normalization. A normalized cDNA library was constructed, containing the cDNAs of interest as shown in Table 1. Only 3 out of the 154 genes listed in Table 1 were targeted genes.

TABLE 1

Prime and Kill Test Results on Rat Liver mRNA

| # | Clone Mega # | | insert size | 80% or more homology to | accession |
|---|---|---|---|---|---|
| 1 | 18 | | 290/290 | brain Ca$^{+2}$-ATPase | J04022 |
| 2 | 19 | | 290 | Protein disulfide isomerase | X02918 |
| 3 | 20 | | 300 262/298 (87%) | Mus-flavin containing | U87147 |
| 4 | 21 | | 300 | female spec Cytp450 exon9 | M33550 |
| 5 | 24 | | 289 | mitochondrial CytB | J01436 |
| 6 | 28 | | 290 | human STS, RAT EST | >gi\|1916369\|gb\|G31644\| |
| 7 | 29 | | 290 | Rat EST | gb\|AI407101\|AI407101 |
| 8 | 30 | | 300 | mRNA for Kan-1 | D43964 |
| 9 | 31 | | 250 | human carboxypeptidase, Rat EST | gb\|AI547958.1\|AI547958 |
| 10 | 34 | | 500 | kallistatin mRNA | U51017 |
| 11 | 33 | | 490 | None | None |
| 12 | 35 | | 400+− | Rat EST | gb\|AI548646\|AI548646 |
| 13 | 36 | | 650 | putative taste receptor | gb\|AF127390\|AF127390 |
| 14 | 37 | | 250 | PEP Kinase | K03248 |
| 15 | 39 | | 590 | β-galactoside-α2,6-sialyltransferase mRNA | M83143 |
| 16 | 44 | | 400 | deoxyribonuclease I | U76635 |
| 17 | 45 | | 340 | apolipoprotein E gene | J02582 |
| 18 | 49 | | 350 | glycine methyltransferase | X06150* |
| 19 | 50 | | 390 | ribosomal protein L30 | K02932 |
| 20 | 52 | | 400 | ribosomal protein L30 mRNA | K02932 |
| 21 | 55 | | 150 | plasma protein | Y11283 |
| 22 | 57 | | 325 | Rat EST | gb\|AI045310.1\|AI045310 |
| 23 | 58 | | 250 | cathepsin B | X82396 |
| 24 | 60 | | 480 | α(1)-inhibitor 3 | X52984 |
| 25 | 61 | | 300 | includes a repeat | |
| 26 | 62 | | 280 | SPI-3 | X16359 |
| 27 | 63 | | 590 | new genes | new genes |
| 28 | 65 | | 550 | sorbitol dehydrogenase | X74593 |
| 29 | 66 | | 330 | RAT EST | gb\|AI717628.1\|AI7I7628 |
| 30 | 67 | | 430 | Rat embryo, placenta EST | gb\|AI230362\|AI230362 |
| 31 | 69 | | 520 | α fibrinogen | X86561 |
| 32 | 70 | | 600 | Rat embryo EST | gb\|AI598398.1\|AI598398 |
| 33 | 75 | | 590 | rat preproalbumin | Targeted gene |
| 34 | 76 | | 450 | ribosomal protein L18 | M20156 |
| 35 | 77 | | 130/130 500 | apolipoprotein E gene | J02582 |
| 36 | 78 | | 500 | same 148 bases to mus and human homogentisate 1,2 dehydrogenase | U58988 |
| 37 | 81 | | 190 | Glut S | Targeted gene |
| 38 | 82 | | 400 | Human ADP-ribosylation factor 3 | gi\|4502202 |
| 39 | 83 | | 680 | ribosomal protein L27a | X52733 |
| 40 | 84 | | 360 | ribosomal protein L28 | X52619 |
| 41 | 85 | | 700 | Glut S A3 subunit (GSTA3) | gb\|AF111160.1\|AF111160 |
| 42 | 86 | | 270 | dC-stretch binding protein | D17711 |
| 43 | 89 | | 470 | rat est brain | gb\|AI412505\|AI412505 |
| 44 | 92 | | 200 | EST: present in embryo, placenta, intestine, kidney etc., | |
| 45 | 93 | | 700 | None | New gene |
| 46 | 2_5 | 5 | 390 | EST | |
| 47 | 2_3 | 3 | 380 | human Cyt C oxidase | gi\|4502990 |
| 48 | 2_4 | 4 | 280 | polyprotein 1-microglobulin/bikunin | gi\|247162\|gb\| |
| 49 | 2_1 | 1 | 250 | ApoCI | X1551 |
| 50 | 2 | 6 | 400 | *M. musculus* CDK-activating kinase | U35249 |
| 51 | 2 | 7 | 360 | Human complement component C6 mRNA | J05064 |
| 52 | 2 | 8 | 400 | Mouse EST | |
| 53 | 2 | 9 | 360 | fatty liver acid binding protein | M35991 |
| 54 | 2 | 12 | 400 | ribosomal protein S10 | X13549 |
| 55 | 2 | 13 | 400 | only one: RAT kidney EST | |
| 56 | 2 | 15 | 380 | est | |
| 57 | 2 | 17 | 390 | EST | |
| 58 | 2 | 52 | 200 | intestinal epithelium proliferating cell-associated mRNA | U21718 |
| 59 | 2 | 19 | 510 | EST | |
| 60 | 2 | 20 | 500 | EST | |
| 61 | 2 | 21 | 480 | Cathepsin H | Y00708** |
| 62 | 2 | 22 | 390 | *M. musculus* serine-rich RNA polymerase suppressor protein | U20619 |
| 63 | 2 | 23 | 690 | U92793 *M. musculus* α glucosidase II α subunit | U92793 |
| 64 | 2 | 25 | 650 | Rat pancreatic amylase mRNA | V01225, J00703 |

TABLE 1-continued

Prime and Kill Test Results on Rat Liver mRNA

| # | Clone Mega # | insert size | 80% or more homology to | accession |
|---|---|---|---|---|
| 65 | 2 | 26 | 550 | EST | |
| 66 | 2 | 27 | 300 | EST | |
| 67 | 2 | 29 | 340 | ribosomal protein L9 | X51706 |
| 68 | 2 | 30 | 550 | pre-α-inhibitor, heavy chain 3 | X83231 |
| 69 | 2 | 31 | 380 | germline MHC class I | L23127 |
| 70 | 2 | 32 | 510 | EST; eye! | |
| 71 | 2 | 34 | 410 | α-1-antitrypsin mRNA | M32247 |
| 72 | 2 | 35 | 440 | Rat, mouse EST | |
| 73 | 2 | 36 | 300 | Rat Kidney ovary EST | NEW GENE |
| 74 | 2 | 37 | 290 | ribosomal protein S8 | X06423 |
| 75 | 2 | 38 | 505 | low quality sequence | |
| 76 | 2 | 39 | 450 | EST highly abundant in many tissues | |
| 77 | 2 | 40 | 410 | Rat EST | |
| 78 | 2 | 41 | 415 | Few Ests | |
| 79 | 2 | 42 | 460 | 157/187 (83%) homology to human heat shock protein | NM_001537.1 |
| 80 | 2 | 43 | 340 | cytoplasmic β-actin gene | J00691 |
| 81 | 2 | 44 | 250 | Mouse plasminogen mRNA | J04766 |
| 82 | 2 | 45 | 460 | 80bp homology to *M. musculus* chromosome 11 EST Rat | AC002324 |
| 83 | 2 | 47 | 650 | *H. sapiens* mRNA (clone C-2k) serine/threonine protein kinase | X80230 |
| 84 | 2 | 48 | 414 | *M. musculus* chromosome 6 homology EST 1 Rat, many mouse | |
| 85 | 2 | 49 | 571 | weak homology to *H. sapiens* mRNA for KIAA0945 protein | NEW GENE |
| 86 | 2 | 50 | 503 | mitochondrial genome | X14848 |
| 87 | 2 | 51 | 347 | regulatory protein (ICLN) mRNA | L26450 |
| 88 | 2 | 18 | 574 | Rnorvegicus mRNA for Bovine C4BP α | Z50051 |
| 89 | 3 | 37 | 366 | none in NR | |
| 90 | 3 | 1 | 641 | α Fibrinogen | X86561, M35601 |
| 91 | 3 | 38 | 388 | *H. sapiens* fibrinogen-like 1 | NM_004467.1 |
| 92 | 3 | 2 | 508 | none in NR | |
| 93 | 3 | 39 | 555 | polyprotein 1-microglobulin/bikunin | S87544 |
| 94 | 3 | 3 | 678 | F1F0 ATPase delta subunit | U00926 |
| 95 | 3 | 4 | 622 | *M. musculus* phenylalanyl tRNA | AF123263.1\|AF123263 |
| 96 | 3 | 41 | 460 | ribosomal Protein L30 | K02932 |
| 97 | 3 | 5 | 489 | Homo sapiens complement component 1r | X04701 |
| 98 | 3 | 42 | 285 | none in NR | |
| 99 | 3 | 6 | 333 | Human and *M. musculus* mRNA for α-2 antiplasmin | Z36774, J02654 |
| 100 | 3 | 43 | 591 | phosphodiesterase I | D28560 |
| 101 | 3 | 7 | 695 | contrapsin-like protease inhibitor | D00751 |
| 102 | 3 | 8 | 555 | PEP kinase | K03248 |
| 103 | 3 | 45 | 688 | Macaca mulatta GST-pi enzyme | L49501 |
| 104 | 3 | 9 | 682 | 45bp homology to *M. musculus* mRNA for synaptobrevin-like Pr | |
| 105 | 3 | 46 | 641 | Monoamine oxidase A | D00688 |
| 106 | 3 | 10 | 567 | *M. musculus* mRNA for transcript overlapping | X67319*** |
| 107 | 3 | 47 | 293 | NADPH-cytochrome P-450 oxidoreductase | M10068, M12516 |
| 108 | 3 | 48 | 586 | RT1.B-1(α)chain of integral membrane protein | X14879 |
| 109 | 3 | 12 | 543 | 45 base to *H. sapiens* mRNA | AL0501281\|HSM800427 |
| 110 | 3 | 49 | 430 | Rat actephase α-1 inhibitor III mRNA | J03552, M28297 |
| 111 | 3 | 13 | 626 | prepro Albumin | Targeted gene |
| 112 | 3 | 50 | 466 | Clathrin light chain (LCA1) | M15882 |
| 113 | 3 | 14 | 259 | 3-α-hydroxysteroid dehydrogenase | M64393 |
| 114 | 3 | 51 | 445 | transthyretin | X14876**** |
| 115 | 3 | 15 | 684 | none in NR | |
| 116 | 3 | 52 | 645 | Partial *Cricetulus griseus* SREBP-2 | U12330 |
| 117 | 3 | 16 | 499 | *M. musculus* flavin-containing monooxygenase | U90535 |
| 118 | 3 | 53 | 674 | none in NR | |
| 119 | 3 | 17 | 459 | none in NR | |
| 120 | 3 | 54 | 454 | none in NR | |
| 121 | 3 | 18 | 572 | none in NR | |
| 122 | 3 | 55 | 539 | Major α-globin mRNA | M17083 |

TABLE 1-continued

Prime and Kill Test Results on Rat Liver mRNA

| # | Clone Mega # | | insert size | 80% or more homology to | accession |
|---|---|---|---|---|---|
| 123 | 3 | 19 | 527 | none in NR | |
| 124 | 3 | 56 | 363 | none in NR | |
| 125 | 3 | 20 | 466 | none in NR | |
| 126 | 3 | 21 | 564 | none in NR | |
| 127 | 3 | 22 | 482 | Partial *M. musculus spindlin* (Spin) mRNA | U48972 |
| 128 | 3 | 23 | 306 | Phosphorylated N-glycoprotein (pp 63) | M29758 |
| 129 | 3 | 60 | 361 | protein disulfide isomerase | X02918 |
| 130 | 3 | 24 | 599 | *M. musculus* mRNA for SAP18 | Z97062 |
| 131 | 3 | 61 | 618 | none in NR | |
| 132 | 3 | 25 | 612 | *M. musculus* mu-crystallin(Crym) | AF039391 |
| 133 | 3 | 62 | 633 | α-methylacyl-CoA racemase mRNA | U89905 |
| 134 | 3 | 26 | 536 | none in NR | |
| 135 | 3 | 63 | 678 | Mouse male-enhanced antigen mRNA (Mea) | M27938 |
| 136 | 3 | 27 | 549 | none in NR | |
| 137 | 3 | 64 | 645 | α-1-macrogloculin mRNA | M84000 |
| 138 | 3 | 28 | 49i | ribosomal protein S9 | X66370 |
| 139 | 3 | 65 | 607 | none in NR | |
| 140 | 3 | 29 | 434 | 27bp to *M. musculus* DNA from BAC 10818 | |
| 141 | 3 | 66 | 601 | Protein kinase C receptor | U03390 |
| 142 | 3 | 30 | 504 | 32bp to *M. musculus* acidic nuclear phospo Pr | |
| 143 | 3 | 67 | 477 | none in NR | |
| 144 | 3 | 31 | 661 | Mitochondrial succinyl-CoA synthetase | J03621 |
| 145 | 3 | 68 | 315 | none in NR | |
| 146 | 3 | 32 | 405 | Rat (diabetic BB) MHC II α | Y00480 |
| 147 | 3 | 69 | 577 | 76bp *H. sapiens cl.* 24643 mRNA | |
| 148 | 3 | 33 | 658 | Rat mRNA for β-globin | X16418, X05080 |
| 149 | 3 | 70 | 440 | Ribosomal protein L23a | X65228 |
| 150 | 3 | 34 | 628 | *M. musculus* Apoc2 gene | Z15090.1 |
| 151 | 3 | 71 | 665 | liver mitochondrial aldehydedehydrogenase | X14977 |
| 152 | 3 | 35 | 645 | none in NR | |
| 153 | 3 | 72 | 565 | *M. musculus* mRNA transcript overlapping myelin basic protein | X67319 |
| 154 | 3 | 36 | 636 | For ribosomal protein S4 | X14210 |

*NOT a gel contaminant, Low copy, *same as 3.72, ****Same as 3.57

EXAMPLE 4

Sample cDNA Libraries

The types of tissues for constructing cDNA libraries are listed in Table 2 below. Typical tissue is composed of one or more major tissue types. Pooled tissues are composed of many cells. An ideal tissue is e.g. liver. "Red." stands for redundancy, "VH" is very high copy, "MC" is medium copy, "LC" is low copy and "LMC" is low medium copy.

TABLE 2

Prime and Kill Method for Constructing cDNA Libraries from Different Types of Tissues

| Genes | Ideal Tissue | Typical Tissue | Pooled Tissues | Cultured Cells |
|---|---|---|---|---|
| # VH | 20+– | 30+– | Many | 20+ |
| % occurrence VH | 60%+ | 30% | 40% | 30%+ |
| # MC | 200+ | 500+ | 2000+ | 500+ |
| Hidden Red. of MC | 15% | 20% | 20% | 20+ |
| # LC, LMC | 20,000 | 20,000 | 40,000+ | 20,000 |
| LC, LMC Red. | 40% | 50% | 40% | 50% |
| Total Red. | 70% | 50%+ | 60%+ | 50% |
| Obvious Red. | 60%+ | 40%+ | Up to 20% | 30–40% |
| Red. N'ized libraries | 50% | 40%+ | 30%+ | 30–40% |
| Red. After VH removal | 15% | 20% | 50%* | 20% |

*Eliminate top 50 high copy genes

EXAMPLE 5

Prime and Kill Method Conventional Mode

Figure 3:
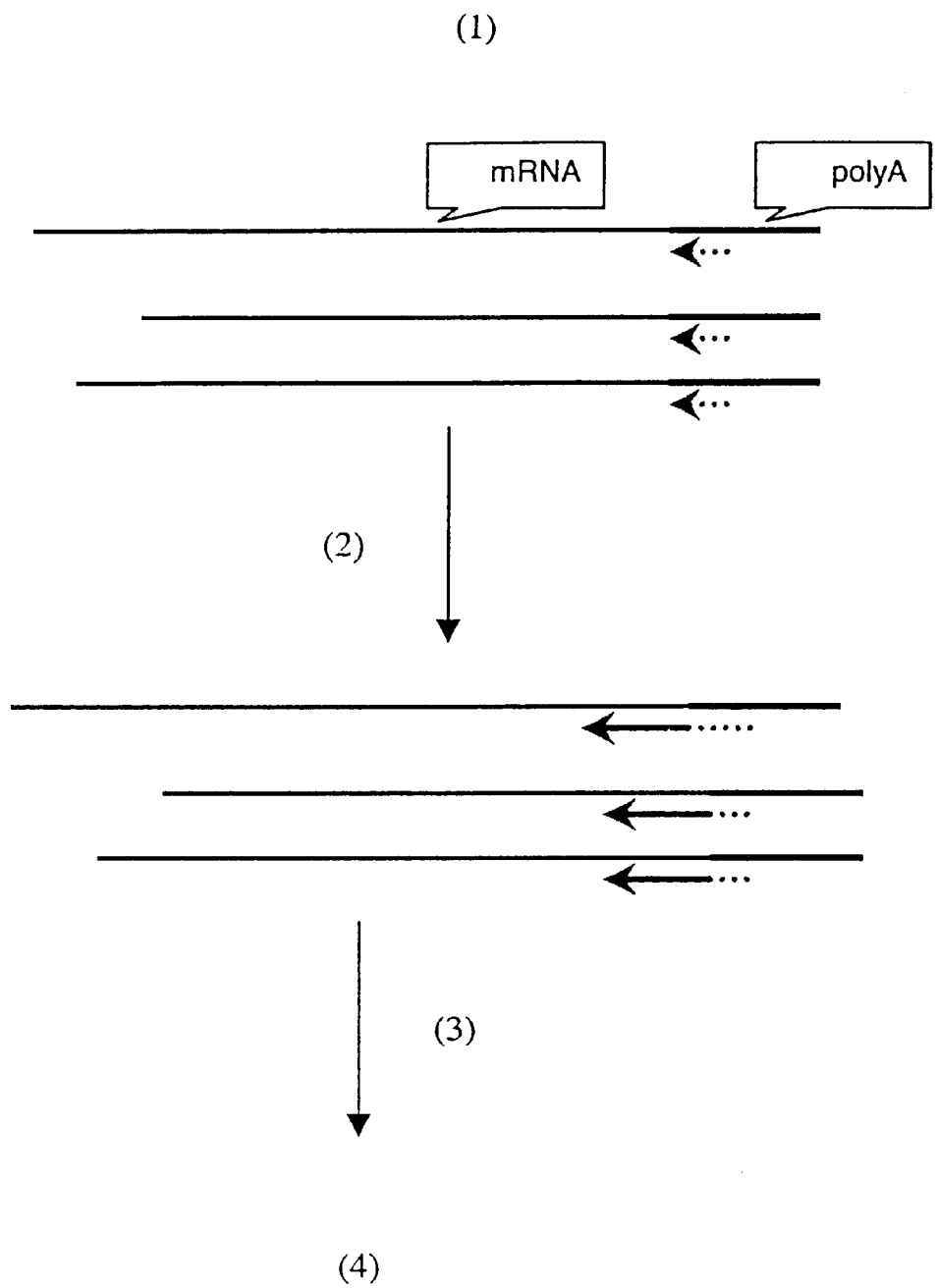
FIG. 3 depicts the conventional normalization mode of the prime and kill method. Arrows with dotted lines represent oligo dT primer (T) 18 and arrows which include solid lines represent short extensions.
  (1) Mixing an excess amount of anchored oligo dT primers to cDNA;
  (2) Creating short extensions at suitable conditions using Reverse Transcriptase;
  (3) Destroying RNA using RNAse A or changing to mild alkaline conditions;
  (4) Purifying short extensions using PCR purification column or phenol chloroform extraction. These short extensions were then used as Killer Primers following the same procedures as described in Killer Primer mode of FIG. 1

The conventional mode is described in FIG. 3. The conventional mode does not require prior knowledge of high copy genes. Briefly, the conventional mode involves synthesis of short first strand DNA extensions on the RNA of interest using random primers or oligo(dT) primers, denaturation and reannealing and destruction of RNA molecules, purification of short first strand cDNA and combination with the same RNA source (for normalization) or combination with another RNA source of interest (for subtraction), addition of E. coli RNAse H, incubation at 37° C. or 42° C., or addition of thermostable RNAse H followed by thermal cycles of denaturation and renaturation and synthesis of cDNA using standard methods, followed by cloning.

Hybridization and Killing Reactions

The RNAse H cycles were carried out using either a Thermostable RNAse H or repeated addition of regular RNAse H. Buffers used included RNAse H buffers, First strand synthesis buffers, and OnePhorAll buffer at 0.5X, 1X and 2X. Additive NaCl and/or DMSO were also used after the first optimization of "control extensions."

Control Extensions

Two 3' end, 50-bp oligos corresponding to two high copy genes (Albumin and Transferrin) were synthesized and diluted to a final concentration equivalent to that of the Killer Primers. Oligo concentrations were varied, ranging from 1, 2, 5 or 10 times in excess of rat liver mRNA. Conditions for complete killing of targeted genes and the presence of non-targeted genes were checked using PCR with forward and reverse primers. Optimal conditions were determined. In order to check the efficiency of killing high copy number genes, assays were performed by measuring the incorporation of a single radiolabeled nucleotide.

EXAMPLE 6

The Conventional Mode for Subtraction

The conventional mode was modified and used for subtraction. Briefly, a large excess of first strand cDNA was added as Killer Primer from one source (driver) to another source (tester). Subsequent addition of thermostable RNAse H or repeated addition of regular RNAse H after heat denaturation subtracted out genes that were expressed in the driver. The assay and methodology were the same as conventional normalization however, more cycles of RNAse H were used for subtraction. This was especially true when the amount of driver was limiting, wherein excess RNAse H reaction cycles were performed.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended claims.

What is claimed is:

1. A method for constructing a normalized cDNA library comprising the steps of:
   (a) identifying and synthesizing oligonucleotides specifically complementary to the 3' region of target mRNA;
   (b) annealing the oligonucleotides of step (a) to a composition comprising non-target RNA and target RNA under conditions sufficient to produce RNA-DNA heteroduplexes specifically between the oligonucleotides and the target RNA;
   (c) cleaving the heteroduplexes with an RNAse H;
   (d) adding oligo(dT) or oligo(dU) primers or a variant thereof that have sequences for a first restriction endonuclease recognition site;
   (e) synthesizing by reverse transcription first-strand cDNA;
   (f) synthesizing second-strand cDNA, producing double-stranded cDNA molecules;
   (g) ligating to both ends of the resulting double-stranded cDNA molecules adapters having cohesive ends of a second restriction endonuclease site which is different from the first restriction endonuclease site;
   (h) removing double-stranded cDNA fragments less than about 150 bp long;
   (i) digesting the remaining cDNA molecules with the first restriction endonuclease;
   (j) digesting the resulting cDNA with the second restriction endonuclease;
   (k) ligating the doubly digested isolated cDNA into a vector predigested with the first and second restriction endonucleases so as to permit cloning of cDNA complementary to the non-target mRNA.

2. The method according to claim 1, wherein the DNA oligonucleotides of step (a) are attached to solid support or biotinylated.

3. The method according to claim 2, wherein the solid support comprises a membrane, a chip, a pin, a bead, a plate, a filter, or a resin.

4. The method according to claim 1, wherein the 3'-region of the target mRNA strand of step (a) is between about 0 and 150 bp.

5. The method according to claim 1, wherein the cDNA fragments less than about 150 bp are removed according to step (h) by gel electrophoresis.

6. The method according to claim 1, wherein the RNAse H of step (c) is from a bacteria, a plant or an animal.

7. The method according to claim 6, wherein the bacteria comprise *E. coli*.

8. The method according to claim 1, wherein the RNAse H of step (c) comprises a thermostable RNAse H.

9. The method according to claim 1 wherein the first restriction endonuclease comprises AscI.

10. The method according to claim 1 wherein the second restriction endonuclease comprises EcoRI or NotI.

11. The method according to claim 1, wherein the cDNA molecules comprise rarely expressed genes.

12. The method according to claim 11, wherein the rarely expressed genes are obtained by targeting and eliminating high copy genes.

13. The method according to claim 11, further comprising amplifying the cDNA molecules.

14. The method according to claim 1, wherein the RNA is obtained from a biological sample from an animal, a plant, a bacterium or a virus.

15. The method according to claim 14, wherein the animal is a human, a dog, a pig, a goat, a sheep, a rabbit or a cow.

* * * * *